US00PP16074P2

(12) United States Plant Patent
Olesen et al.

(10) Patent No.: US PP16,074 P2
(45) Date of Patent: Oct. 25, 2005

(54) ***CLEMATIS* PLANT NAMED 'EVIPO033'**

(50) Latin Name: *Clematis viticella*
Varietal Denomination: Evipo033

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 78 days.

(21) Appl. No.: 10/897,918

(22) Filed: Jul. 23, 2004

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new *Clematis* cultivar which is well suited to propagation in glasshouses. With a tall growth habit, profuse, deep red-purple flowers and continuous summer flowering. The variety successfully propagates from softwood cuttings and is suitable for cultivation in commercial glasshouses. This new and distinct variety has shown to be uniform and stable in the resulting generations from asexual propagation.

3 Drawing Sheets

Botanical classification: *Clematis l.* Genus—*Clematis*. Species—*viticella*.
Variety denomination: 'Evipo033'.

SUMMARY OF THE DISCOVERY

The present invention constitutes a new and distinct variety of *Clematis* which originated from a naturally occurring branch mutation of *Clematis viticella* 'Kermesina' a non-patented variety. The new variety is named 'Evipo033'.

The main difference between 'Evipo033' and its parent is the presence of inner 'ruff' of petaloid stamens at the flower center. Where as the flower center of 'Kermesina' has few dark colored anthers and filaments, 'Evipo033' has 50 or more petaloid stamens.

The objective of the selection of this *Clematis* variety for commercial glasshouse and nursery culture was to create a new and distinct variety with unique qualities that this variety has:

1. Profuse red-purple flowers;
2. Reliable and repeatable production plant;
3. Summer flowering;
4. Good disease resistance.

These qualities required improvement in *Clematis* varieties that were in commercial cultivation and the objectives have been substantially achieved in the new variety, as evidenced by the unique combination of characteristics that are present in 'Evipo033', which distinguish it from all other varieties of which we are aware.

The mutation was selected from the parent plant in a controlled environment. As a result, 'Evipo033' was selected by Raymond J. Evison and Mogens N. Olesen in their *Clematis* development program in Domarie Vineries Les Sauvagees, St. Sampsons, Guernsey, Channel Islands, United Kingdom in June 1996.

Asexual reproduction of 'Evipo033' by cuttings was first done by Raymond J. Evison and Mogens N. Olesen in Domarie Vineries Les Sauvagees, St. Sampsons, Guernsey, Channel Islands, United Kingdom in April 1997. This initial and subsequent asexual propagations have demonstrated that the characteristics of 'Evipo033' are true to type and are transmitted from one generation to the next.

BRIEF DESCRIPTION OF THE DRAWING

The accompanying color illustrations show as true as is reasonably possible to obtain in color photographs of this type:

FIG. 2.2 Stem showing branching and the attachment of leaves and flowers;

FIG. 2.3 Flower bud closed and at various stages of opening;

FIG. 2.4 Stem showing attachment of mature and juvenile leaves.

DETAILED DESCRIPTION OF THE VARIETY

Figure 1:
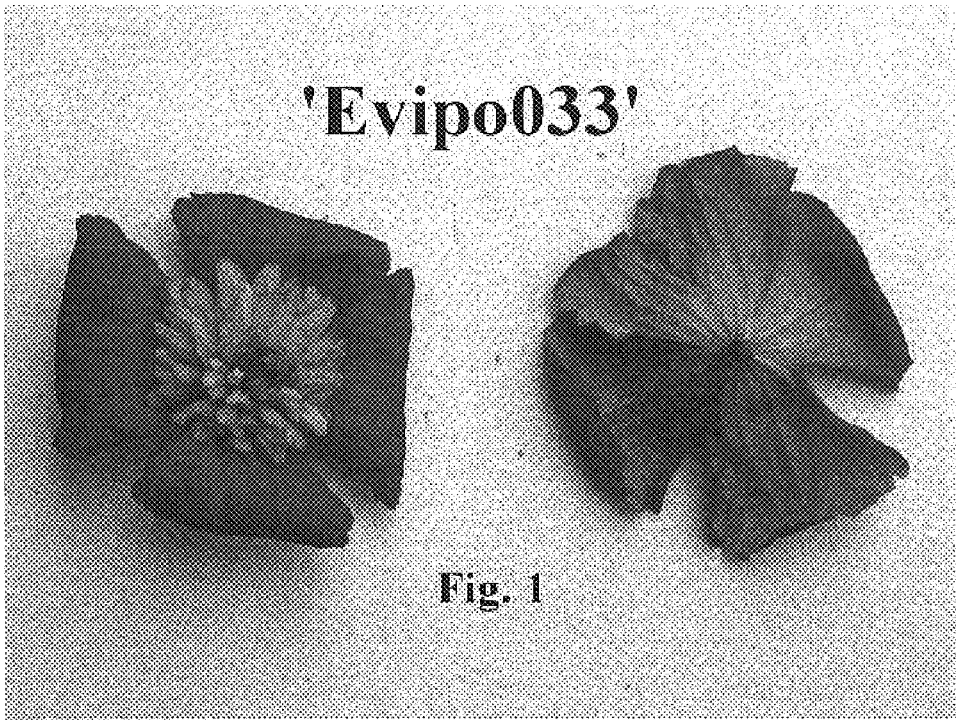
FIG. 1 Enlarged image of open flower, upper and lower surface.

The following is a detailed description of 'Evipo033', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing *Clematis* variety is 'Kermesina', a non-patented variety. Chart 1 details several physical characteristics of 'Evipo033' and the comparison variety.

CHART 1

| | 'Evipo033' | 'Kermesina' |
|---|---|---|
| Flower center/ reproductive organs | Center consists of an inner 'ruff' of 50 or more petaloid stamens. | Flower center consists of a small boss of dark colored anthers. |

FLOWER AND FLOWER BUD

Blooming habit: Summer flowering. Normal flowering months are May, June, July, August, September.

Flower bud:

*Size.*—12 to 15 mm in length. Bud diameter is 7 mm.

*Bud form.*—Ovate to elliptical.

*Bud color.*—Yellow-Green Group 146C and Greyed-Purple Group 186B at ¼ opening.

Peduncle:

*Aspects.*—Droops at 45 degrees and holds the flower facing downwards (nodding).

*Surface.*—Smooth.

*Length.*—125 to 160 mm average length.

*Color.*—Yellow-Green Group 146D changing to Purple Group N79A to N79B as the flower opens.

*Strength.*—Moderate.

Receptacle: Absent.

Flower arrangement:

*Location on vine.*—Flower buds develop on new growth.

*Borne.*—Compound cyme cluster of 3 to 5 flowers.

Flower bloom:

*Size.*—45 to 50 mm in diameter. 15 mm in depth.

*Profile.*—Upon opening: Flowers are flat. After opening: Flowers are flat with tepals reflexing somewhat.

*Tepal color.*—Upon opening: Upper surface is Red-Purple Group 61A in color. After opening: Upper surface is Red-Purple Group 72B in color. Lower surface is slightly lighter, Red-Purple Group 72B to Red-Purple Group 72C. Venations the color of Red-Purple Group 72B observed.

*Variations.*—Distinct coloration at the tepal base on both upper and lower surfaces is White Group 155C.

*Fragrance.*—None.

*Lasting quality on plant.*—20 to 25 days.

*Lasting quality as a cut flower.*—6 to 10 days.

Tepals:

*Quantity.*—Normally 4 tepals. Occasionally 5 or 6 tepals observed.

*Size.*—28 to 30 mm in length by 23 to 25 mm wide.

*Shape.*—Individual tepal shape is obovate.

*Undulation of margin.*—Weakly serrated.

*Tepal apex.*—Cuspidate.

*Recurvature of tip.*—Reflexed somewhat.

*Persistence.*—Tepals drop off cleanly leaving inner 'ruff' of petaloid stamens.

*Arrangement.*—Tepals are arranged regularly.

Reproductive organs:

*Arrangement.*—Compact.

*Pollen.*—Quantity: None.

*Anthers.*—Size: 3 mm in length. Color: Red-Purple Group 61B. Quantity: 45 to 60.

*Filaments.*—Color: Yellow-Green Group N150C. A secondary group of stamens extends from the center of the flower on its own peduncle, which is 20 to 30 mm long and carries a whirl of 5 to 10 stamens. Length: 7 mm.

*Pistils.*—None observed.

Seed head characteristics: None observed. Flowers are sterile.

PLANT

Plant form: Climbing.

Size: Seasons growth attains 2.5 to 3 meters in height. Average spread is 1 to 1.5 meters.

Hardiness: Trials to date show the variety is cold tolerant to USDA Cold Hardiness Zone 4.

Stems:

*Color.*—Young wood: Yellow-Green Group 145A. Older wood: Greyed-Orange 166B.

*Internodes.*—Shape: Cylindrical. Length: 70 to 120 mm.

*Surface.*—Young wood: Smooth and pubescent. Older wood: Smooth and pubescent.

Plant foliage:

*Leaf characteristics.*—Deciduous.

*Mature leaf form.*—Normally trifoliate. However, 5 to 7 leaflets arranged in pinnate form have been observed.

*Compound leaf size.*—120 to 160 mm (l )×75 to 90 mm (w).

*Abundance.*—Normally 20 leaves per 150 mm of stem.

*Mature leaf color.*—Upper surface is Green Group 141C. Lower surface is Green Group 141B.

*Juvenile leaf color.*—Upper surfaces are Yellow-Green Group 141C. Lower surfaces are Yellow-Green Group 141D.

Plant leaves and leaflets:

*Stipules.*—Absent.

*Petioles.*—Average length: 75 to 100 mm. Color: Yellow-Green Group 144A. Clasping: By leaf petiole.

*Petioloule.*—Length: 5 to 10 mm. Color: Yellow-Green Group 144B.

*Leaflet shape.*—General shape: Ovate to elliptical. Base: Rounded. Apex: Obtuse to acute. Margin: Entire.

*Leaflet size.*—35 to 40 mm in length by 17 to 22 mm wide.

*Leaflet texture.*—Upper side: Smooth. Lower side: Smooth. Pubescence: Not observed. Thickness: Moderate. Glossiness: Moderately Glossy Finish.

Disease resistance: Subject to any disease that normally attacks the species, however the variety is more tolerant to Botrytis, *Phoma clematadina*, and root diseases such as Theilaviopsis than some *Clematis*.

We claim:

1. We claim a new and distinct variety of *clematis* plant named 'Evipo033', described and illustrated herein, due to its abundant red-purple flowers, attractive long-lasting foliage and repeatable flowering under glasshouse conditions, suitability for production from softwood cuttings in pots, durable flowers and foliage which make the variety suitable for distribution in the floral industry.

* * * * *

Figure 2:
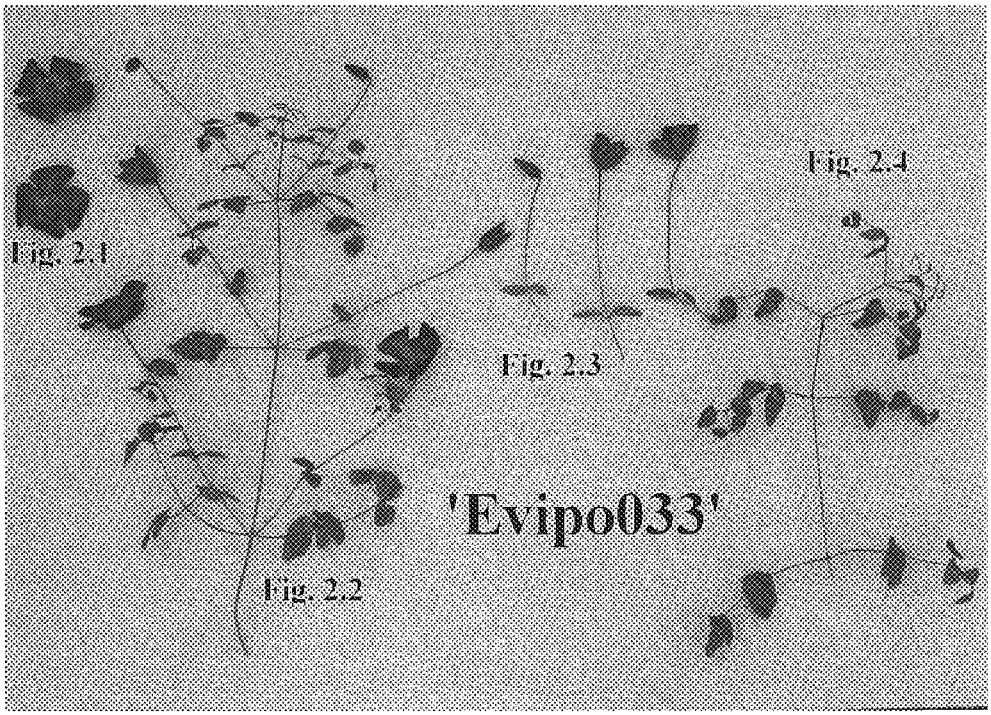
FIG. 2.1 Open flower, upper and lower surface.
Figure 3:
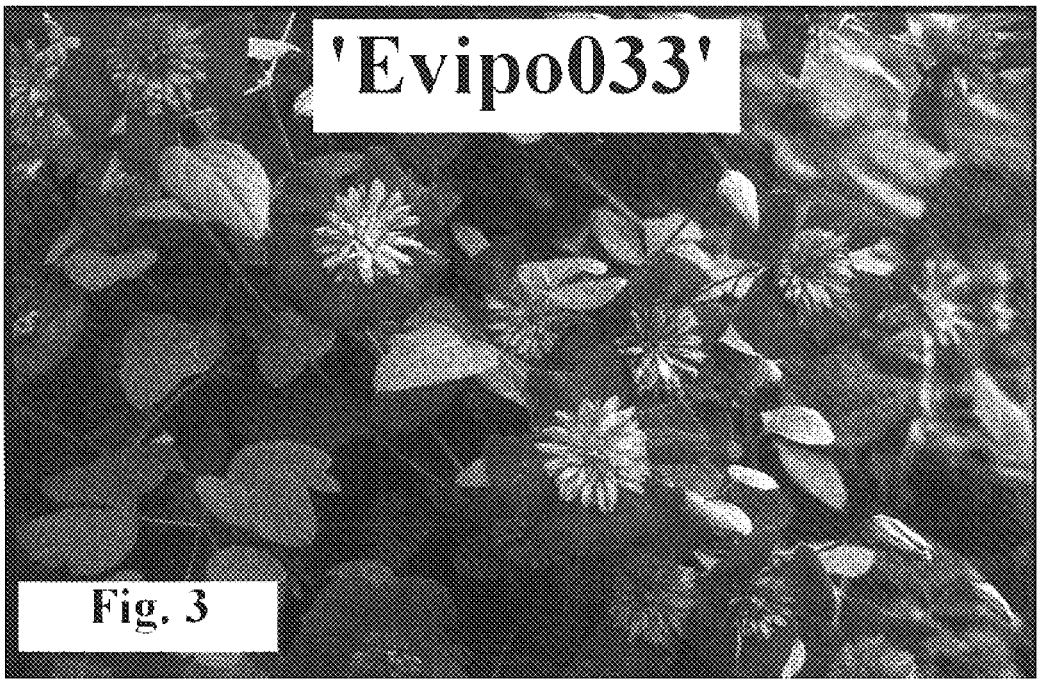
FIG. 3 Leaves, flower buds, and cluster of flowers showing peduncle aspect.

Fig. 2.1
Fig. 2.2
Fig. 2.3
Fig. 2.4
'Evipo033'